United States Patent [19]

Soled et al.

[11] Patent Number: 5,113,034

[45] Date of Patent: May 12, 1992

[54] DIMERIZATION CATALYST AND PROCESS THEREFOR

[75] Inventors: Stuart L. Soled, Pittstown; Nicholas C. Dispenziere, Jr., Wall; Ramzi Y. Saleh, Flemington; Sabato Miseo, Pittstown, all of N.J.

[73] Assignee: Exxon Research and Engineering Company, Florham Park, N.J.

[21] Appl. No.: 740,251

[22] Filed: Aug. 5, 1991

[51] Int. Cl.$^5$ .............................................. C07C 2/04
[52] U.S. Cl. .................................. 585/510; 585/515; 585/520; 585/526; 585/530
[58] Field of Search ............... 585/510, 515, 520, 526, 585/530

[56] References Cited

U.S. PATENT DOCUMENTS 4,476,343  10/1984  Johnson .............................. 585/530
4,511,750  4/1985   Miller ................................. 585/515

FOREIGN PATENT DOCUMENTS 1155125  6/1969  United Kingdom .

OTHER PUBLICATIONS

Sohn et al, "High Catalytic Activity of NiO-TiO$_2$/-SO$_4^{2-}$ for Ethylene Dimerization", J. Catalysis, 101, pp. 428-433 (1986).
Sohn et al, "New Syntheses of Solid Catalysts for Ethylene Dimerization", J. Molecular Catalysis, 41, pp. 375-378 (1987).

Primary Examiner—Patrick P. Garvin
Assistant Examiner—E. D. Irzinski
Attorney, Agent, or Firm—Jay Simon

[57] ABSTRACT

A solid, acid catalyst, supported or unsupported, comprised of an anion modified Group IVB oxide is used to dimerize $C_3$ or $C_4$ containing feedstreams.

7 Claims, No Drawings

DIMERIZATION CATALYST AND PROCESS THEREFOR

FIELD OF THE INVENTION

This invention relates to a liquid phase process for dimerizing $C_3$ and $C_4$ olefins over a catalyst comprising an anion modified Group IVB oxide.

BACKGROUND OF THE INVENTION

The dimerization of $C_3$ and $C_4$ olefin is well known and practiced commercially, e.g., with phosphoric acid on kieselguhr or with nickel oxide on silica-alumina. While these catalysts are adequate, they have substantial drawbacks. Thus, the former is difficult to prepare and activate and can form a difficult to remove cement-like deposit in the reactor. The latter makes $C_8$ paraffins, which in a chemicals environment have virtually no value. Consequently, a desire exists for an easily prepared and activated catalyst that exhibits a low selectivity to paraffins at high conversion rates.

Strong acid catalysts such as bulk sulfated materials, $NiO/TiO_2/SO_4$, have been reported as active ethylene polymerization catalysts, Sohn, J. R., Kim, H. W., and Kim, J. T., J. Mol. Catalysis, 41, 375 (1987), and Sohn, J. R. and Kim, H. J., J. Catal., 101, 428 (1986). Nevertheless, the art recognizes that polyethylene catalysts are not necessarily useful as catalysts for polymerizing or dimerizing higher olefins.

SUMMARY OF THE INVENTION

In accordance with this invention, $C_3$ or $C_4$ olefins are dimerized in a liquid phase process at elevated temperature and autogenous pressure in the presence of a catalyst comprising an anion modified Group IVB oxide (titania, zirconia, or hafnia). The anion modifier may be a sulfate or tungstate, the Group IVB oxide may be supported on a refractory metal oxide, and nickel oxide may also be employed as a dispersed phase on the solid acid, with or without the support.

The process described herein has low selectivity to saturated dimers, e.g., less than about 5% $C_8$ or $C_6$ paraffins, preferably less than about 3% $C_8$ or $C_6$ paraffins. While selectivity to the desired $C_6$ or $C_8$ product olefins usually decreases as conversion increases, this process can readily be operated at 80%+conversion of the $C_3=$ or $C_4=$ selectivities of 50%+ to the desired dimers.

The process is a heterogeneous process, the feed and products being liquid, the catalyst being a solid acid. Acid strengths, measured by Hammett Acidity Function, Ho, range from about $-14.5$ to about $-16.5$. Temperatures can preferably range from about 110° C.-180° C. with autogenous pressure. The reaction is usually effected in a fixed bed or continuously stirred reactor and continued for a period sufficient to provide the desired level of conversion, e.g., 1-4 hours. The desired dimers of $C_3=$ or $C_4=$ are easily recovered, e.g., by distillation.

In accordance with the present invention, anion modified Group IVB oxides, preferably zirconium or titanium oxides are incorporated, i.e., impregnated or dipped, with a sulfate or tungstate precursor thereof to form the catalyst used in the present invention. Suitable sources of the oxide include salt solutions, such as zirconium or titanium oxychlorides, nitrates, and tetrachlorides. The salt solution is preferably water soluble and capable of forming a hydroxide precipitate upon the addition of a base. Suitable bases include but are not limited to ammonium hydroxide or alkylammonium hydroxide which are added in order to adjust the pH of the solution in the range from about 9 to about 11, thereby facilitating the formation of the hydroxide precipitate.

Alkoxides may also be employed for preparing the catalysts, e.g., zirconium n-propoxide, titanium i-propoxide, and titanium tertiary butoxide, these being hydrolyzed with water to form the hydroxide precipitate.

Any material capable of forming sulfate or tungstate when calcined with the Group IVB oxide may be used to provide the sulfate or tungstate, e.g., hydrogen sulfide, sulfur dioxide, mercaptans and sulfur- and halo-containing compounds such as fluoro-sulfonic acid, sulfuryl chloride or thionyl chloride, or mixtures thereof, or ammonium meta tungstate, etc.

The anion can be incorporated with the hydroxide or oxide by any one of several known methods. For example, a zirconium hydroxide or oxide, can be immersed in an aqueous solution containing sulfuric acid, or the sulfate could be incorporated with the oxide by impregnating the hydroxide or oxide with a sulfate solution, preferably, ammonium sulfate followed by drying at about 100° C.-150° C.

After the sulfate or tungstate source has been incorporated with the hydroxide or oxide and dried, calcination is carried out, preferably in an oxidizing atmosphere or one that will allow conversion to the sulfate or tungstate, at temperatures of about 450° C. to about 650° C. for the sulfate and 450° C. to 800° C. for the tungstate, preferably at about 500° C. to about 600° C. for about 0.5-30 hours, preferably about 1-24 hours. In the most preferred embodiment calcination is carried out at about 600° C. for about 0.5 to about 10 hours in air.

The concentration of the sulfate or tungstate concentration remaining on the catalyst after calcination preferably ranges from about 3.0 wt% to about 5.0 wt%, based on the weight of Group IVB metal oxide.

Alternatively, the hydroxide can be first calcined at temperatures ranging from 450° C. to 650° C. to convert the hydroxide to the oxide, the sulfate or tungstate being incorporated as previously mentioned.

Of the Group IVB oxides, zirconia and titania are preferred, titania being particularly preferred; of the anion modifiers the sulfate is preferred.

A surface NiO phase may be added to the anion modified oxide by preparing an aqueous slurry containing the anion modified Group IVB oxide and a nickel salt, e.g., the nitrate, and increasing the pH of the slurry to about 7, e.g., by adding a base such as 1 molar ammonium carbonate. The slurry solids are then filtered, washed, dried and calcined as previously mentioned. The amount of nickel oxide dispersed on the anion modified Group IVB oxide is about 0.5-5.0 wt%; for every 11 m²/g of surface area of the oxide, preferably about 0.5 to 1.5 wt% NiO. The anion modified solid acid Group IVB oxide, with or without a dispersed surface nickel oxide phase, can be further supported on a refractory metal oxide support. Any known refractory metal oxide used as a catalyst support may be employed, preferably silica, alumina, or silica-alumina, most preferably silica.

The supported catalyst may be formed by heating at 60° C.-90° C. a water slurry of silica added to an aqueous solution of zirconium oxynitrate and urea. The zirconium salt deposits on the silica and is then dried and calcined as previously mentioned. Catalyst loadings for supported catalysts may range from about 1%–25% by weight of catalyst.

EXAMPLES

Preparation of Zr(OH)$_4$

Take 360 grams of ZrOCl$_2$·H$_2$O and dissolve in 2800 cc of water. Slowly add concentrated ammonium hydroxide solution (~14M) with stirring. A precipitate will appear; continue adding the ammonium hydroxide until the pH of the final slurry reaches ~10. Let the solution sit for two hours. The precipitate is filtered, washed with distilled water twice, and then with water containing a sufficient quantity of ammonium hydroxide to have a pH of 10. To help remove any residual chloride remaining, the solid is then reslurried into a 1M solution of ammonium hydroxide, the solution is heated to 60° C., stirred, and after one hour filtered and washed with water. Finally, the solid is dried at 110° C. overnight.

Preparation of ZrO$_2$/SO$_4$ 10 grams of Zr(OH)$_4$ dried at 110° C. are placed into 22 cc of the 1M sulfuric acid solution, stirred for 5 minutes, and filtered. The solid is then dried overnight at 100° C. This material is then calcined at 600° C. for hours in air.

Preparation of ZrO$_2$/WO$_3$ 25 grams of Zr(OH)$_4$ dried at 110° C. is placed into 40 cc of an aqueous solution containing 4.8 grams of ammonium metatungstate, stirred for 5 minutes, and filtered. The solid is then dried overnight at 110° C. This material is then calcined at 600° C. for 3 hours in air.

Preparation of 10% NiO/ZrO$_2$/SO$_4$ 18 grams of ZrO$_2$/SO$_4$ calcined at 600° C. was prepared as described above. 7.79 grams of nickel nitrate was dissolved in 30 cc of water, and the ZrO$_2$/SO$_4$ was added to the solution. The slurry was heated to 90° F. A solution of 1 molar ammonium carbonate was added dropwise to the slurry until the pH reached 7. The solid was filtered, washed dried at 100° C. overnight and calcined at 600° C. for 3 hours.

Preparation of 24% ZrO$_2$/SO$_4$/SiO$_2$ 50 grams of Davison #62 silica is calcined at 600° C. overnight. This is added to a solution containing 26.3 grams of zirconium oxynitrate, 26.4 grams of urea and the slurry is stirred for 6 hours at 90° C. The pH of the solution increases from ~2.5 to 6.5 during this treatment. The solid is then filtered, washed with water and dried at 110° C. 25 grams of this dried material is then dipped into 55 grams of a 1N H$_2$SO$_4$ solution, stirred for 5 minutes and filtered. It is dried at 110° C. overnight and then a portion is calcined at 600° C. for 3 hours.

Preparation of 25% NiO/24% ZrO$_2$/SO$_4$/SiO$_2$ 10.4 gm of nickel nitrate is dissolved into 200 cc of water. To the solution we add 8.0 gm of the 24% ZrO$_2$/SiO$_2$/SO$_4$ (dried 110° C.) described above. The slurry is stirred, heated to 90° F. and a 1 molar ammonium carbonate solution is added until a pH of 7 is reached. The slurry is stirred for an additional 30 minutes, after which the solid is filtered, washed with water, and dried at 110° C. and heated to 600° C. for 3 hours.

Preparation of 28% NiO/SiO$_2$·Al$_2$O$_3$

Conventional Catalyst 24 grams of Davison #62 silica is calcined at 600° C. overnight. This is added to a solution containing 36.3 grams of nickel nitrate in 36 cc of water. This is heated to 90° F. and a solution containing 18.2 grams of ammonium carbonate in 90 cc of water is added dropwise until a pH of 7 is reached. This is stirred for 30 minutes, filtered washed with water and dried at 110° C. overnight. The material is calcined at 600° C. overnight.

Preparation of Ti(OH)$_4$ 240 gms of water are placed in a flask and immersed in an ice bath. Once the water is cooled to ~2° C., it is added slowly to 150 gm of TiCl$_4$, keeping the solution at near 0° C. After stirring for an hour, sufficient solution of concentrated NH$_4$OH is added to raise the pH to 10. A precipitate forms which is aged 24 hours and then filtered and washed with water. To help remove any residual chloride remaining, the solid is then reslurried into a 1M solution of ammonium hydroxide, the solution is heated to 60° C., stirred, and after 1 hour filtered and washed with water. Finally the solid is dried at 110° C. overnight.

Preparation of TiO$_2$/SO$_4$ 20 gms of Ti(OH)$_4$ (dried 110° C.) are placed into 43 gm of 1N H$_2$SO$_4$, stirred for 5 minutes, filtered and dried at 110° C. The material is calcined at 600° C. for 3 hours.

EXAMPLE 1

The sulfate catalysts were calcined at 600° C. and the tungstate catalyst at 800° C., 0.5–1 hour in air immediately prior to charging, and then loaded into an autoclave along with a known amount of decane and trans-butene-2 (feed).

Powdered catalyst, calcined at 600° C. for sulfate sodified and 800° C. for tungstate modified for 0.5 to 1 hour in air were loaded into the autoclave along with 7.2 gm decane and 70.1 gm trans-butene-2 feed. The feed comprised 99.4% trans-2-butene, 0.4% butane, 0.1% butene-1 and 0.1% cis-butene-2, was added to a 300 cc Parr reactor through a trap containing activated 13x mole sieve. The feed was maintained in a liquid state by cooling the feed to 0° C. with a cooling coil. The autoclave was equipped with a heating mantle and a variable speed stirrer.

The autoclave was maintained under autogeneous nitrogen pressure while being heated for five hours. The residence time (RT) defined as:

$$RT = \frac{\text{weight of catalyst (g)} \times \text{reaction time (hours)}}{\text{weight of butene (g)}}$$

varied with the weight of the catalyst. The autoclave was heated to temperatures ranging from about 95° C. to about 220° C. The autoclave was sampled at one hour periods during the run. At the end of the run, the autoclave was then chilled to 5° C. and liquid samples of the reaction product were recovered. The samples were hydrogenated over a 0.5 wt% Pt/Al$_2$O$_3$ catalyst before being analyzed. The hydrogenated samples were then passed to gas chromatography columns in order to determine the degree of conversion, product selectivity, isomer distribution and the degree of branching of the hydrogenated octene fraction.

|  | 28% NiO/SiO$_2$—Al$_2$O$_3$ | 10% NiO/ZrO$_2$/SO$_4$ |
| --- | --- | --- |
| RUN 1 |  |  |
| Temp., °C. | 95 | 95 |
| Residence Time. | .22 | .22 |
| % Conversion (end of run) | 43 | 77 |
| RUN 2 |  |  |
| Temp., °C. | 125 | 125 |
| Residence Time. | .34 | .34 |
| % Conversion (end of run) | 60 | 96 |
| RUN 3 |  |  |
| Temp., °C. | 175 | 175 |
| Residence Time. | 1.0 | .75 |
| % Conversion (end of run) | 80 | 99 |

Under all conditions, the sulfated catalyst was more active.

EXAMPLE 2

28% NiO/SiO$_2$-A$_2$O$_3$ and TiO$_2$/SO$_4$ were compared at comparable conversions, since the selectivity is conversion dependent.

|  | TiO$_2$/SO$_4$ | 28% NiO/SiO$_2$.Al$_2$O$_3$ |
| --- | --- | --- |
| Temperature, °C. | 125 | 175 |
| Res. Time. Hour | .34 | 1 |
| % Conversion | 84 | 88 |
| % Cracking (C$_{5-7,9-11}$) | 14.7 | 11.5 |
| % C$_8$ sel | 45.9 | 41.6 |
| % C$_{12}$ | 20.4 | 26.4 |
| % C$_{16}$ | 10.5 | 12.7 |
| % C$_{20}$ | 4.7 | 5.8 |
| % C$_8$ sat. | 2.8 | 5.8 |
| Branching | 2.1 | 1.2 |

This example shows that TiO$_2$/SO$_4$ is both more active and at similar conversion C$_8$ selectivity slightly higher,
less C$_{12}$-C$_{16}$ and C$_{20}$, slightly more C$_{5-7}$ and C$_{9-11}$, and most importantly lower C$_8$ saturates. The TiO$_2$/SO$_4$ has more highly branched products.

EXAMPLE 3

This example compares the variation of C$_8$ paraffin selectivity as a function C$_8$ yield for TiO$_2$/SO$_4$ and NiO on silica alumina.

|  | TiO$_2$/SO$_4$ | | | 28% NiO/SiO$_2$.Al$_2$O$_3$ | |
| --- | --- | --- | --- | --- | --- |
| Temperature, °C. | 95 | 125 | 220 | 125 | 175 |
| Res. Time. Hour | .6 | .34 | .22 | .34 | 1.0 |
| Conversion | 72 | 84 | 76 | 64 | 88 |
| C$_8$ Yield | 42.5 | 38.6 | 34.5 | 39.8 | 36.6 |
| C$_8$ Sats | 1.00 | 2.80 | 3.5 | 2.2 | 5.8 |

As the severity of the reaction is increased by increasing either temperature or residence time, the C$_8$ yield falls off for both catalysts. However, as the C$_8$ yield decreases the percent of C$_8$ saturates increases more rapidly for the nickel on silica alumina catalyst than for the sulfated titania.

What is claimed is:

1. A process for dimerizing C$_3$ or C$_4$ olefins comprising reacting a feed stream containing C$_3$ or C$_4$ olefins or mixtures thereof in the liquid phase with a catalyst consisting essentially of an anion modified Group IVB oxide, wherein the anion is a sulfate or a tungstate.

2. The process of claim 1 wherein the reaction is carried out at a temperature ranging from 110° C.-180° C.

3. The process of claim 1 wherein the Group IVB oxide is zirconia or titania.

4. The process of claim 1 wherein the catalyst is supported on a refractory metal oxide.

5. The process of claim 4 wherein the support is silica, alumina, or silica-alumina.

6. The process of claim 2 wherein at least about 80% of the feed stream is converted and the selectivity to the dimer is at least about 50%.

7. The process of claim 6 wherein the selectivity to saturated dimers is less than about 5%.

* * * * *